(12) United States Patent
Holland et al.

(10) Patent No.: US 10,434,607 B2
(45) Date of Patent: Oct. 8, 2019

(54) METHOD TO IMMOBILIZE AN ENTRAPPED CONTAMINANT WITHIN A HONEYCOMB STRUCTURE

(71) Applicant: United Technologies Corporation, Hartford, CT (US)

(72) Inventors: Brian K. Holland, Lansing, MI (US); William Bogue, Hebron, CT (US); Jeffrey Denton, Jackson, MI (US)

(73) Assignee: United Technologies Corporation, Farmington, CT (US)

( * ) Notice: Subject to any disclaimer, the term of this patent is extended or adjusted under 35 U.S.C. 154(b) by 798 days.

(21) Appl. No.: 14/909,323

(22) PCT Filed: Jul. 29, 2014

(86) PCT No.: PCT/US2014/048607
§ 371 (c)(1),
(2) Date: Feb. 1, 2016

(87) PCT Pub. No.: WO2015/017405
PCT Pub. Date: Feb. 5, 2015

(65) Prior Publication Data
US 2016/0175988 A1  Jun. 23, 2016

Related U.S. Application Data

(60) Provisional application No. 61/861,196, filed on Aug. 1, 2013.

(51) Int. Cl.
*B23K 31/02* (2006.01)
*G01N 21/94* (2006.01)
*F01D 5/00* (2006.01)
*F02K 1/78* (2006.01)
*G01N 21/3563* (2014.01)
(Continued)

(52) U.S. Cl.
CPC ............ *B23K 31/02* (2013.01); *F01D 5/005* (2013.01); *F02K 1/78* (2013.01); *G01N 21/3563* (2013.01); *G01N 21/94* (2013.01); *F05D 2230/232* (2013.01); *F05D 2230/40* (2013.01); *F05D 2300/133* (2013.01); *F05D 2300/174* (2013.01); *F05D 2300/701* (2013.01);
(Continued)

(58) Field of Classification Search
None
See application file for complete search history.

(56) References Cited

U.S. PATENT DOCUMENTS 4,065,322 A   12/1977   Langford
5,443,658 A   8/1995    Hermanek
(Continued)

OTHER PUBLICATIONS

Extended EP Search Report dated Aug. 3, 2016.
(Continued)

*Primary Examiner* — Eric W Golightly
(74) *Attorney, Agent, or Firm* — O'Shea Getz P.C.

(57) ABSTRACT

A method of immobilizing a contaminant within a component includes identifying the contaminant. The component is thermally processed via a specific thermal cycle related to the contaminant. The specific thermal cycle is performed within an inert environment relative to a substrate. The specific thermal cycle is configured to effect a controlled evaporation of volatiles of the contaminant and a controlled coking of remaining contaminant.

9 Claims, 6 Drawing Sheets

(51) Int. Cl.
  *G01N 21/552* (2014.01)
  *G01N 21/35* (2014.01)
(52) U.S. Cl.
  CPC ... *G01N 21/552* (2013.01); *G01N 2021/3595* (2013.01); *G01N 2201/0221* (2013.01)

(56) References Cited

U.S. PATENT DOCUMENTS

| | | | |
|---|---|---|---|
| 5,482,645 A * | 1/1996 | Maruyama | C11D 1/667 |
| | | | 134/40 |
| 5,536,805 A | 7/1996 | Kangas | |
| 5,561,827 A | 10/1996 | Reeves et al. | |
| 5,626,988 A | 5/1997 | Daniel-Ivad et al. | |
| 5,952,042 A | 9/1999 | Rafferty et al. | |
| 6,328,810 B1 | 12/2001 | Conner et al. | |
| 6,402,866 B1 | 6/2002 | Casey et al. | |
| 6,589,600 B1 | 7/2003 | Hasz et al. | |
| 6,612,480 B1 | 9/2003 | Rafferty | |
| 6,797,759 B1 | 9/2004 | Ellison et al. | |
| 2004/0216535 A1 * | 11/2004 | Brostmeyer | G01M 15/14 |
| | | | 73/865.6 |
| 2004/0238596 A1 | 12/2004 | Ellison et al. | |
| 2006/0091182 A1 | 5/2006 | Ivory et al. | |
| 2009/0026182 A1 | 1/2009 | Hu et al. | |
| 2009/0165926 A1 | 7/2009 | Stadtlander et al. | |
| 2009/0188748 A1 | 7/2009 | Stevenson et al. | |
| 2012/0206717 A1 | 8/2012 | Witz et al. | |
| 2017/0144259 A1 * | 5/2017 | Yu | B23K 9/0026 |

OTHER PUBLICATIONS

EPO Official Letter dated Mar. 31, 2017 for Application No. 14832816.4.
Martin A. Elliott: "Chemistry of Coal Utilization: Second Supplementary Volume/Prepared Under the Guidance of the Committee on Chemistry of Coal Utilization", Jan. 1, 1981 (Jan. 1, 1981), Wiley, New York, XP055357798, ISBN: 978-0-471-07726-8, pp. 665-670.

* cited by examiner

METHOD TO IMMOBILIZE AN ENTRAPPED CONTAMINANT WITHIN A HONEYCOMB STRUCTURE

CROSS-REFERENCE TO RELATED APPLICATION

This application claims priority to PCT Patent Application No. PCT/US14/048607 filed Jul. 29, 2014, which claims priority to U.S. Provisional Patent Application No. 61/861,196 filed Aug. 1, 2013.

BACKGROUND

This disclosure relates generally to immobilization of an entrapped contaminant and, more particularly, to a weld repair.

Titanium alloys have been of considerable interest in many applications due to their highly desirable performance characteristics. Among other things, they provide low density, high strength, fatigue resistance, corrosion resistance, and good strength-to-weight ratio. Titanium alloys have been of benefit in many environments, including aerospace.

Due in part to these highly desirable performance characteristics, aerospace components with a titanium honeycomb and skins are commonly utilized in areas that may be subjected to various fluids and high temperatures. Normal operations may result in damage to the components requiring repair processing at temperatures which may cause the service fluids and the titanium to chemically interact. There are often considerable economic incentives to repair these components by methods such as welding, brazing or wide-gap brazing. Fluid penetration from service use, cleaning, or manufacture/repair processing, however, may complicate these repairs, especially components with honeycomb structure which have limited or no access for conventional cleaning methods.

SUMMARY

A method of immobilizing a contaminant within a component, according to one disclosed non-limiting embodiment of the present disclosure, includes identifying the contaminant. The method also includes thermally processing the component via a specific thermal cycle related to the contaminant.

In a further embodiment of the present disclosure, the identifying of the contaminant includes comparing a measured spectrum to a predetermined spectrum.

In a further embodiment of any of the foregoing embodiments of the present disclosure, the method also includes performing the specific thermal cycle above an evaporation temperature of the contaminant but below an alpha case formation temperature.

In a further embodiment of any of the foregoing embodiments of the present disclosure, the method also includes performing the specific thermal cycle within an inert environment relative to a substrate.

In a further embodiment of any of the foregoing embodiments of the present disclosure, the method also includes: removing a test section from the component; and thermally processing the test section with the component.

In a further embodiment of any of the foregoing embodiments of the present disclosure, the method also includes confirming thermal cleaning via the test section.

In a further embodiment of any of the foregoing embodiments of the present disclosure, the method also includes destructive testing the test section.

In a further embodiment of any of the foregoing embodiments of the present disclosure, the component further includes an internal honeycomb and the fluid contaminant disposed within the internal honeycomb.

A method of repairing a component, according to another disclosed non-limiting embodiment of the present disclosure, includes: immobilizing a contaminant within the component; and weld repairing the component subsequent to immobilizing the contaminant.

In a further embodiment of any of the foregoing embodiments of the present disclosure, the method also includes immobilizing the contaminant within the component via thermal cleaning.

In a further embodiment of any of the foregoing embodiments of the present disclosure, the method also includes: identifying the contaminant with Fourier Transform Infrared Spectroscopy; and immobilizing the contaminant within the component via a specific thermal cycle related to the contaminant.

In a further embodiment of any of the foregoing embodiments of the present disclosure, the method also includes performing the specific thermal cycle above an evaporation temperature of the contaminant but below the alpha case formation temperature.

In a further embodiment of any of the foregoing embodiments of the present disclosure, the method also includes performing the specific thermal cycle within an inert environment relative to a substrate.

In a further embodiment of any of the foregoing embodiments of the present disclosure, the method also includes removing a test section from the component prior to thermally processing the test section with the component.

In a further embodiment of any of the foregoing embodiments of the present disclosure, the method also includes confirming thermal cleaning via the test section.

In a further embodiment of any of the foregoing embodiments of the present disclosure, the method also includes destructive testing the test section.

In a further embodiment of any of the foregoing embodiments of the present disclosure, the component further includes an internal honeycomb and the fluid contaminant is disposed within the internal honeycomb.

An aerospace component, according to another disclosed non-limiting embodiment of the present disclosure, includes a honeycomb structure with a thermally decomposed contaminant and a weld repair.

In a further embodiment of any of the foregoing embodiments of the present disclosure, the honeycomb structure is manufactured of titanium.

In a further embodiment of any of the foregoing embodiments of the present disclosure, the aerospace component is an outer sleeve of an exhaust nozzle.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
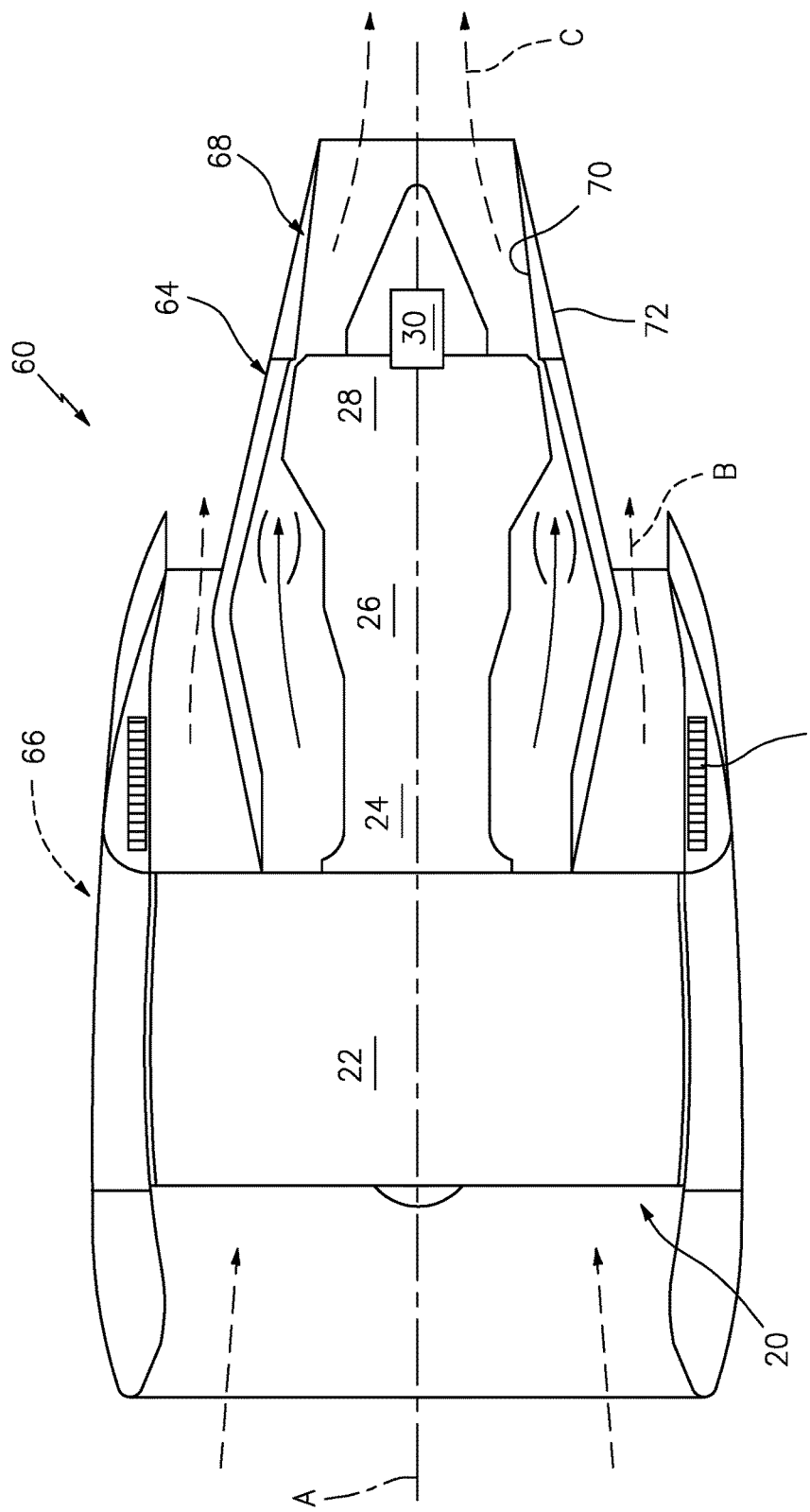
FIG. 1 is a schematic cross-section of a nacelle assembly for a high bypass gas turbine engine.

FIG. 1 schematically illustrates a gas turbine engine 20. The gas turbine engine 20 is disclosed herein as a two-spool turbo fan that generally incorporates a fan section 22, a compressor section 24, a combustor section 26 and a turbine section 28. Generally, the fan section 22 drives air along a bypass flowpath and into the compressor section 24. The compressor section 24 drives air along a core flowpath for compression and communication into the combustor section 26, which then expands and directs the air through the turbine section 28.

The gas turbine engine 20 is received within a nacelle assembly 60, to establish a bypass flow path B and a core flow path C. A thrust reverser 62 (illustrated schematically) may be located within the nacelle assembly 60 for selective deployment into the bypass flow path B to provide a thrust reversing function. Although depicted as a turbofan in the disclosed non-limiting embodiment, it should be understood that the concepts described herein are not limited to use with turbofans as the teachings may be applied to other types of turbine engines as well as other structures, for example, but not limited to low bypass engine case structures.

Figure 2:
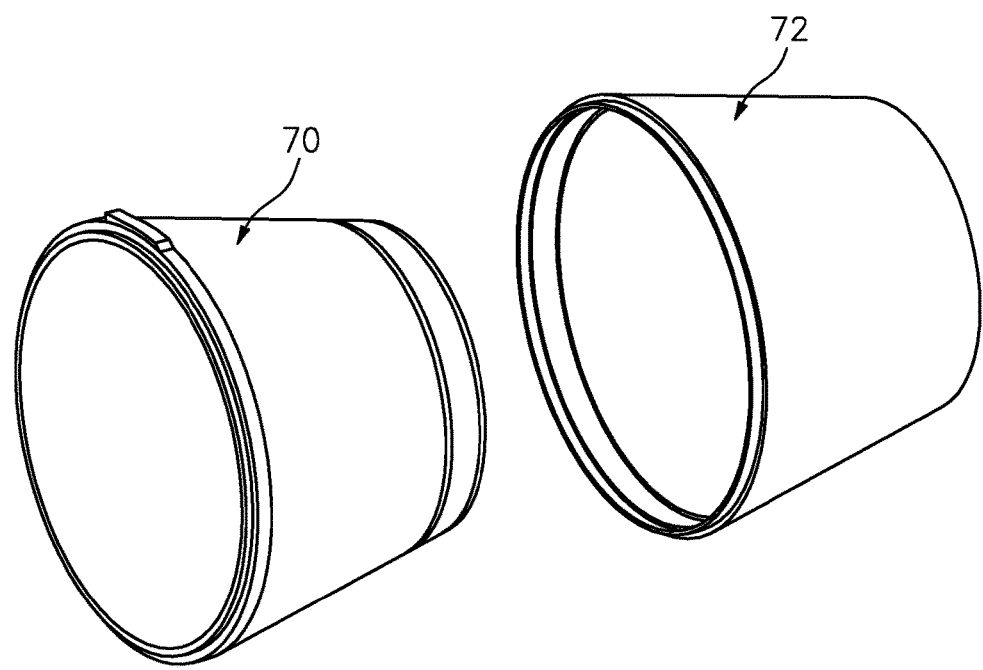
FIG. 2 is a perspective view of an aerospace component represented as an exhaust duct of the nacelle assembly.
Figure 3:
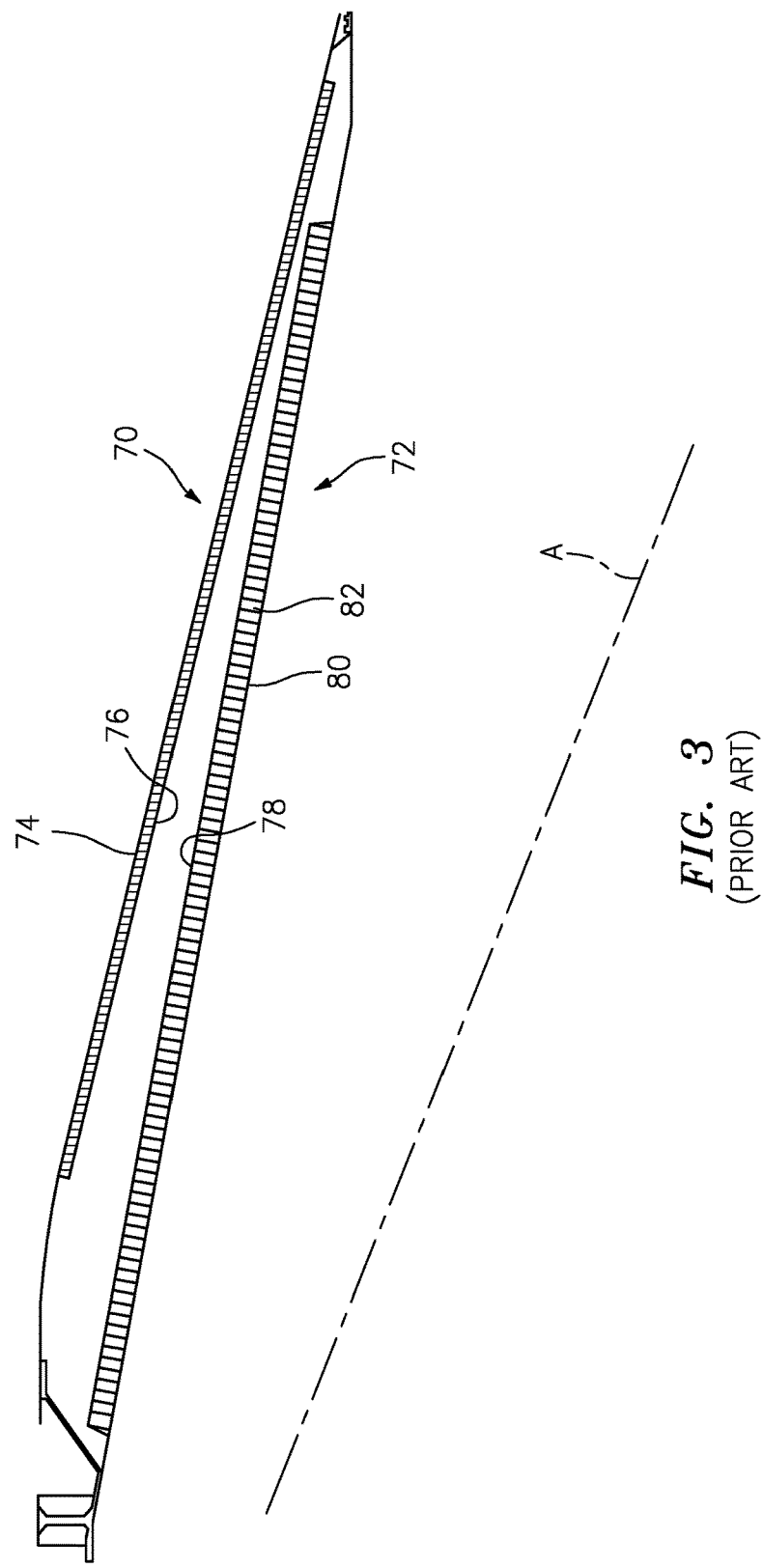
FIG. 3 is a cross-sectional view of an outer sleeve for the exhaust duct.

The example nacelle assembly 60 includes a core nacelle 64 at least partially surrounded by a fan nacelle 66. The core nacelle 64 typically includes an exhaust nozzle 68. The exhaust nozzle 68 in the disclosed non-limiting embodiment includes an inner sleeve 70 and an outer sleeve 72 typically manufactured of titanium alloy (also shown in FIG. 2). Referring to FIG. 3, the inner sleeve 70 generally includes a perforated inner skin 74 and an outer skin 76 while the outer sleeve 72 generally includes an inner skin 78 and an outer skin 80 with a honeycomb structure 82 therebetween. It should be appreciated that various other components, materials and constructions thereof will also benefit herefrom.

Under some operational conditions, a contaminant such as oil from, for example, a bearing compartment 30 (illustrated schematically in FIG. 1) may escape through worn seals as the engine cools and pool on the inner sleeve of the exhaust nozzle 68. It should be appreciated that other bearing compartments in other engine locations, as well as other engine architectures may also be subject to fluid penetration. Furthermore, although oil is utilized as the example contaminant herein, other contaminates inclusive of, but not limited to, oil byproducts, kerosene based fuels, glycols, polyalkylinglycols (PAG), transmission fluids, cleaning fluids etc., as well as mixtures thereof may also be at issue. Oil also frequently coagulates and can pick up particulate debris and form a generally non-"fluid" layer such as typically described as "grime" which may be considered contaminants as defined herein. In addition, other contaminants typical of manufacturing processes, may also be considered contaminants as defined herein.

With reference still to FIG. 3, the perforated inner skin 74 facilitates the evaporation of the example oil contaminant from within the inner sleeve 70 during engine operation, however, thermal cycling of the oil and the exhaust nozzle 68 may cause thermal stress that may lead to cracks in the outer skin 76. Once the oil penetrates the inner sleeve 70, especially via a puncture or crack damage, the oil or contaminant pools on or inside the outer sleeve 72. The outer sleeve 72 is not perforated, so the oil remains trapped between the inner sleeve outer skin 76 and the inner skin 78 of the outer sleeve 72. The outer sleeve may then crack due to the same thermal cycling such that oil may further penetrate into the honeycomb structure 82. The oil within the honeycomb structure 82 may thereby impair weld repairs of the outer sleeve 72.

Figure 4:
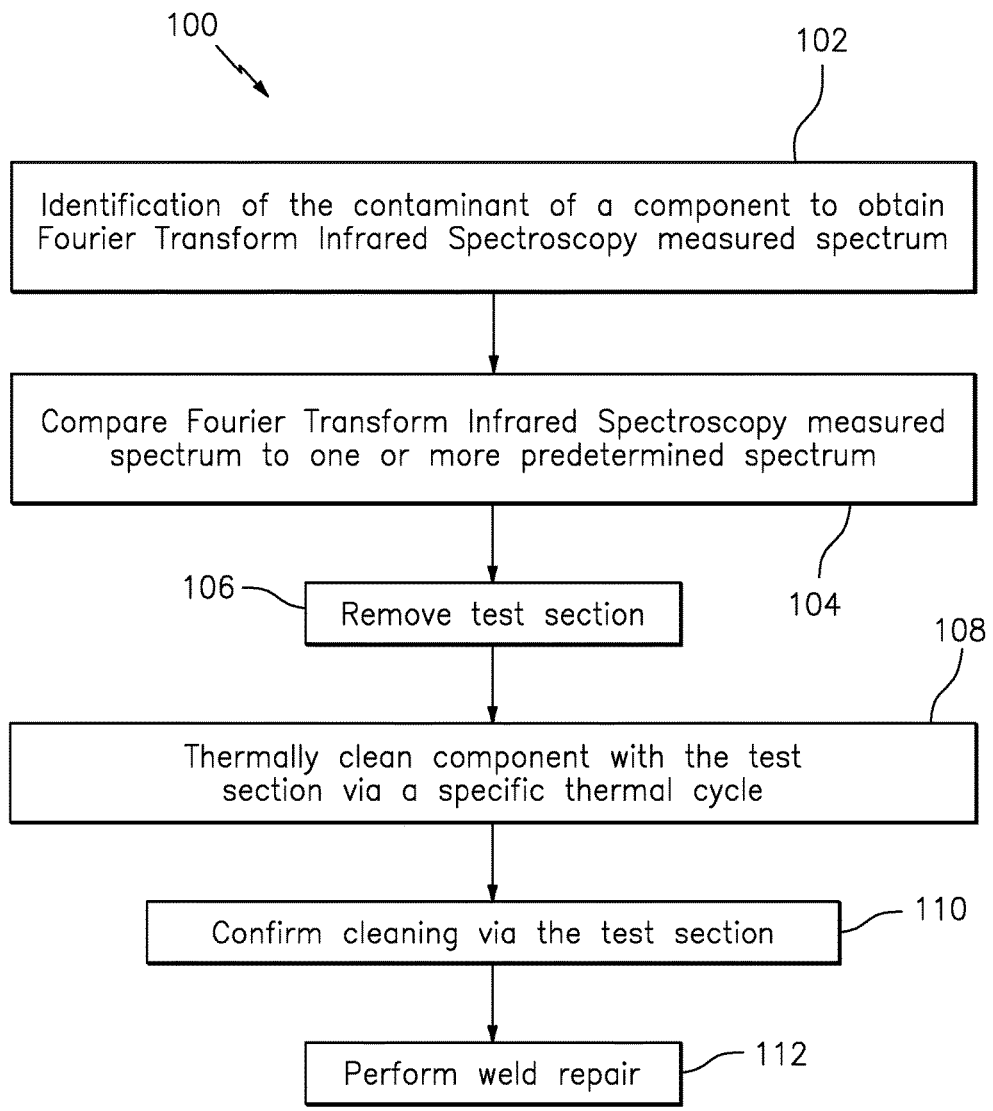
FIG. 4 is a block diagram of a method to immobilize an entrapped fluid.

With reference to FIG. 4, a method 100 to immobilize an entrapped contaminant, according to one disclosed non-limiting embodiment, initially includes identification of the fluid contaminant (step 102). It should be appreciated that although the outer sleeve 72 is utilized in this disclosed non-limiting embodiment, other components with an entrapped contaminant will also benefit herefrom, especially those where the fluid entrapment is not accessible by conventional cleaning methods.

Figure 5:
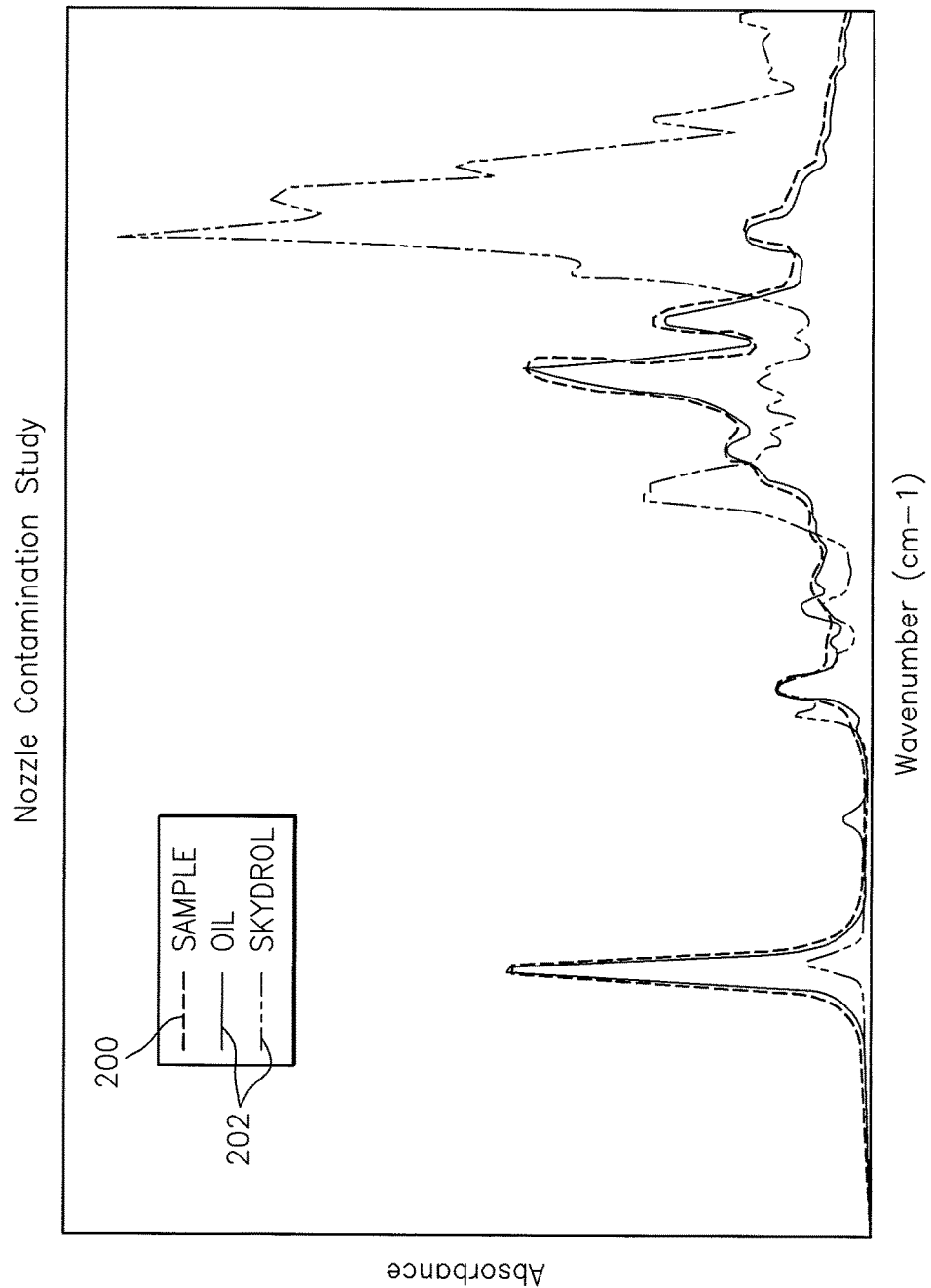
FIG. 5 is a graphical representation of a scan from Fourier Transform InfraRed (FTIR) spectroscopy.

Identification of the fluid contaminant may proceed via a scan from, for example, a Fourier Transform InfraRed (FTIR) spectroscopy to obtain a measure spectrum 200 (see FIG. 5). A hand-held FTIR unit such as 4200 FlexScan Series FTIR manufactured by Agilent Technologies of Santa Clara, Calif, USA can expedite the process through performance of an on-site assessment of the contaminants in situ. It should be appreciated that other identification systems inclusive of but not limited to, Thermal Gravimetric Analysis (TGA), Chromatography, Inductively Coupled Plasma (ICP) and/or other such chemical identification process that provides the desired chemical identification.

In one example, the Fourier Transform Infrared Spectroscopy (FTIR) inspection of the contamination utilizes a Spherical Diamond ATR probe, and a ZnSe crystal with a scan of wave numbers ranging from 4000-800 $cm^{-1}$ with a minimum of 32 scans per spectra with 2 to 3 representative spectra measured per contaminant sample. The 2 to 3 representative measured spectra are cross-compared to ensure accurate sampling and proper technique. That is, the 2-3 representative spectra assure a proper spectrum is obtained. The 2-3 representative spectra are taken to ensure the accuracy of the spectra from each sample. They are then cross-compared to ensure their fidelity. This is performed on the actual part samples and on the control species, oil, skydrol, etc. before used as qualification data. Each "scan" or "spectra" using FTIR actually scans the sample 32 times before recording/reporting a spectra. This can be adjusted from 16 up to 150 depending on the user's discretion, type of sample and ambient environmental conditions. For example, field scans of an unknown material in an uncontrolled environment typically require the higher number of scans to ensure relevant and accurate spectra.

The measured spectrum 200 is then compared to one or more control spectra 202 (FIG. 5) to identify the contaminant(s) such as gear oil or hydraulic fluid (step 104) in the chemical fingerprint wave number range of 2000-800 $cm^{-1}$. Chemical fingerprint is determined by peak locations, relative signal intensity at those locations and peak to peak ratios between unique identifiers. The 4000-2000 $cm^{-1}$ need not be used as it does not present unique chemical identifiers to distinguish between organic compounds. Contaminants or mixtures thereof that are specifically identified may then be thermally processed to clean for weld repair as further described. That is, the weld repair is performed with specific regard to the identified contamination.

In one non-limiting example, certain characteristic peaks are identified in the scanned spectrum, if those peaks align with or are centered on specific wave numbers within the spectrum that correspond to a specific contamination, then that contamination is 'identified' in that test section. With the suspected presence of contaminant mixtures, a correlated range of mixtures is used as the reference, or a second analysis technique, especially chromatography or TGA may be used.

Figure 6:
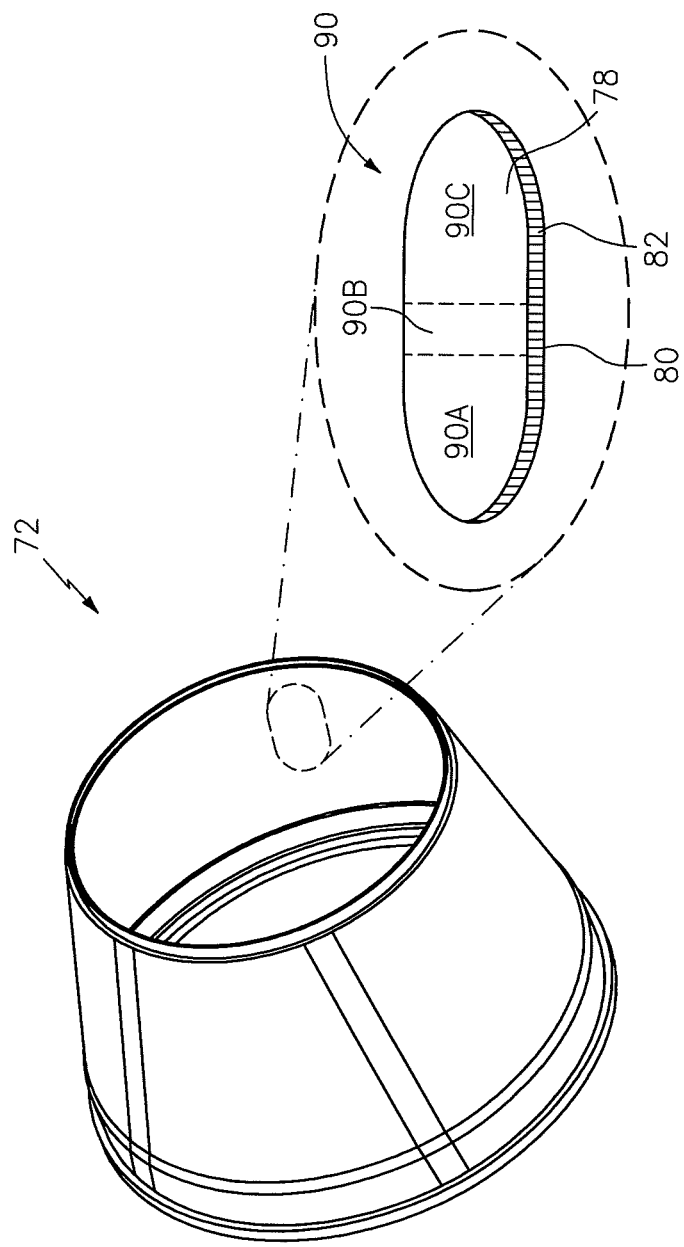
FIG. 6 is a perspective view of an exhaust duct with a test sample removed.

A test section 90 is then removed (step 106; see FIG. 6). This test section 90 may then be further segmented 90A, 90B, 90C to provide multiple samples for multiple tests. The test section 90 may be from a damaged area which is to be weld repaired.

The outer sleeve 72 is then thermally processed with the section 90 (step 108) via a specific thermal cycle. The specific thermal cycle is used to perform a controlled evaporation of the volatiles and a controlled coking of remaining contaminants. Consideration is given to accessibility of the entrapped contaminant(s) whereby additional venting holes are created and/or damage is locally removed to facilitate gas flowpath to relieve pressure variants caused by thermal cycling. The specific thermal cycle is performed at a heating rate to mitigate pressure variants, and a temperature above the evaporation temperature of the contaminant but below the alpha case formation temperature of the parent substrate, such as titanium, and/or thermal limitation criteria of other substrates, e.g. high temperature steel(s). That is, the temperature of the specific thermal cycle should be limited to prevent chemical reaction between contaminant and substrate. Alpha case is typically an alpha-stabilized enriched phase occurring on titanium and its alloys when exposed to heated air or oxygen. Alpha case is brittle, and tends to be prone to micro-cracking of the substrate which reduces the parent substrate's performance and its fatigue properties. Alpha case can be avoided by processing in a vacuumed environment. Additionally, pressure and/or vacuum may be used to mitigate internal pressure variants of bonded components and/or lower evaporation temperatures of the contaminant(s).

Controlled evaporation typically maintains the pressure increase from evaporation to not exceed the rate at which the pressure can be released from the component. The heating rate, external pressure and any additionally installed venting paths may be used to facilitate the controlled evaporation—in the case of the welded patch, the open hole for the patch also operates as a vent.

The specific thermal cycle is determined, in part, by the type of contaminant identified via FTIR analysis in step 104. The specific thermal cycle is performed at a temperature above an evaporation temperature of the contaminant but below the alpha case formation temperature or the temperature at which the contaminant chemically reacts with or diffuses in to the substrate. Alpha case is an oxygen-enriched phase that may be of particular concern on titanium and its alloys when exposed to heated air or oxygen or in the presence of carbon sources. Alpha case is brittle, and tends to be prone to microcracks which propagate in—to the substrate and will reduce the metal's performance and its fatigue properties. Alpha case can be avoided by processing in a vacuumed or inert environment. Vacuum has additional advantage when the dominant cleaning requirement can be accomplished by controlled evaporation.

The thermal processing may be performed within a furnace having an inert atmosphere of, for example, Argon at temperatures of 700-750 F (371-400 C) for a titanium alloy component. The internal honeycomb cells are thereby saturated with inert gas sufficient to prevent formation of deleterious alpha case. It should be appreciated that other temperatures and environments may be utilized for substrates other than titanium. Typically, the furnace is cleaned after each contaminant soaked component is thermally processed or stress relieved.

For the example gear oil soaked outer sleeve 72, the volatile evolution and coking processes from the specific thermal cycle do not result in excessive pressures within the honeycomb 82 due to pressure communication features in the honeycomb. The remaining coked oil is condensed (semi-evaporated state)) and thermally decomposed to reduce or prevent weld line intrusion thereby negating porosity, low-notch toughness and brittleness effects at the weld line typically caused by aforementioned contaminants. The interior surfaces of at least one test section 90 may then be tested by metallographic methods (step 110). The testing is performed to, for example, ensure there is no alpha case, oxygen rich layer, or soft alpha beyond predetermined limits for a sound weld. It should be appreciated that various tests including destructive tests may be performed.

The outer sleeve 72 is then weld repaired (step 112). It should be appreciated that other repairs may also then be performed without degradation of the skins, honeycomb or weldments. Components subject to such contaminants are thereby readily weld repaired due to the immobilization of the contaminants.

It should be appreciated that although the method is described with respect to the example outer sleeve 72, the method may be utilized with different thermal cycles for other fluids or other substrates beyond titanium to immobilize entrapped contaminants within various components and thereby permit weld or braze repairs to be performed. Other components include but are not limited to Lower Aft Pylon Fairings of similar substrates where such contaminants exist.

Although the different non-limiting embodiments have specific illustrated components, the embodiments of this invention are not limited to those particular combinations. It is possible to use some of the components or features from any of the non-limiting embodiments in combination with features or components from any of the other non-limiting embodiments.

It should be understood that relative positional terms such as "forward," "aft," "upper," "lower," "above," "below," and the like are with reference to the normal operational attitude of the vehicle and should not be considered otherwise limiting.

It should be understood that like reference numerals identify corresponding or similar elements throughout the several drawings. It should also be understood that although a particular component arrangement is disclosed in the illustrated embodiment, other arrangements will benefit herefrom.

Although particular step sequences are shown, described and claimed, it should be understood that steps may be performed in any order, separated or combined unless otherwise indicated and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be understood that within the scope of the appended claims, the disclosure may be practiced other than as specifically described. For that reason the appended claims should be studied to determine true scope and content.

What is claimed is:

1. A method of repairing a component, the method comprising:
    immobilizing a contaminant within the component;
    thermally processing the component via a specific thermal cycle related to the contaminant; and
    weld repairing the component subsequent to immobilizing the contaminant;
    wherein the specific thermal cycle effects a controlled evaporation of volatiles of the contaminant and a controlled coking of remaining contaminant.

2. The method as recited in claim 1, further comprising immobilizing the contaminant within the component via thermal cleaning.

3. The method as recited in claim 1, further comprising:
    identifying the contaminant with Fourier Transform Infrared Spectroscopy; and
    immobilizing the contaminant within the component via a specific thermal cycle related to the contaminant.

4. The method as recited in claim 3, further comprising performing the specific thermal cycle above an evaporation temperature of the contaminant but below an alpha case formation temperature of the component.

5. The method as recited in claim 4, further comprising performing the specific thermal cycle within an inert environment relative to a substrate.

6. The method as recited in claim 5, further comprising removing a test section from the component prior to thermally processing the test section with the component.

7. The method as recited in claim 6, further comprising confirming thermal cleaning via the test section.

8. The method as recited in claim 6, further comprising destructive testing the test section.

9. The method as recited in claim 1, where the component further comprises an internal honeycomb and wherein the contaminant includes a fluid contaminant disposed within the internal honeycomb.

* * * * *